United States Patent
Dorogi et al.

(10) Patent No.: US 8,758,809 B2
(45) Date of Patent: *Jun. 24, 2014

(54) SKIN TREATMENT COMPOSITIONS CONTAINING COPPER-PIGMENT COMPLEXES

(75) Inventors: Peter Ladislaus Dorogi, Easton, PA (US); David Bruce Vasily, Bethlehem, PA (US); John Patrick McCook, Frisco, TX (US)

(73) Assignee: CHL Industries, LLC, Frisco, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/813,791

(22) Filed: Jun. 11, 2010

(65) Prior Publication Data

US 2010/0247630 A1   Sep. 30, 2010

Related U.S. Application Data

(63) Continuation of application No. 11/320,280, filed on Dec. 28, 2005, now abandoned.

(51) Int. Cl.
*A61K 9/127* (2006.01)

(52) U.S. Cl.
USPC .......................................... 424/450; 424/401

(58) Field of Classification Search
CPC .. A61K 9/127; A61K 9/1271; A61K 9/12772
USPC ................................................. 424/450, 401
See application file for complete search history.

(56) References Cited

U.S. PATENT DOCUMENTS

| | | | | |
|---|---|---|---|---|
| 8,298,555 B2 * | 10/2012 | McCook et al. | ............... | 424/401 |
| 8,303,985 B2 * | 11/2012 | Dorogi et al. | .................. | 424/450 |
| 2003/0004499 A1 * | 1/2003 | McDaniel | ........................ | 606/3 |
| 2004/0018237 A1 * | 1/2004 | Perricone | ........................ | 424/484 |
| 2005/0261750 A1 * | 11/2005 | McDaniel | ........................ | 607/86 |
| 2006/0110439 A1 * | 5/2006 | Tobia et al. | .................... | 424/450 |

OTHER PUBLICATIONS

Touitou et al in Pharmaceutical Sciences, vol. 83, # 9, Sep. 1994, pp. 1189-1203.*

* cited by examiner

*Primary Examiner* — Gollamudi Kishore
(74) *Attorney, Agent, or Firm* — Louis C. Paul

(57) ABSTRACT

A therapeutic method is described in which copper is delivered into the skin as a complex with sodium chlorophyllin. Sodium copper chlorophyllin is encapsulated in suitable lecithin-type liposomes, containing a high concentration of linoleic acid and having diameters in the range 150-350 nanometers. The method provides therapeutic benefits in the treatment of environmentally-induce premature skin aging, excessively oily skin, acne and acne-related skin disorders, acne-rosacea, and also stimulates the natural tanning response of skin to sunlight and other ultraviolet-containing radiation.

3 Claims, No Drawings

SKIN TREATMENT COMPOSITIONS CONTAINING COPPER-PIGMENT COMPLEXES

CROSS-REFERENCE TO RELATED APPLICATION

This application is a continuation of U.S. application Ser. No. 11/320,280 filed Dec. 28, 2005 now abandoned and titled "Skin Treatment Compositions Containing Copper-Pigment Complexes". The disclosure of the above-mentioned application is incorporated herein by reference in its entirety.

FIELD OF THE INVENTION

This invention is directed toward therapeutic substances and methods for treating skin problems caused by environmental factors or chronic skin pathologies.

BACKGROUND OF THE INVENTION

There are important roles for copper in regulating various functions and processes in the human body, including within the skin. Copper is part of an enzyme that regulates energy metabolism, cytochrome c oxidase, and is also essential for the repair of skin tissues by virtue of its role in the cross-linking of elastin and collagen by lysyl oxidase. Copper is a key part of the skin's antioxidant protection system, for removal of superoxide radicals by the antioxidant SOD (superoxide dismutase). Studies have shown that when copper salts are applied directly to the skin in an aqueous solution there is little or no significant benefit. Moreover, the cuprous copper ion ($Cu^{+2}$) is a catalyst for activating molecular oxygen and is therefore a potential pro-oxidant. It is therefore of interest to develop methods that deliver copper to the skin and net therapeutic results, yet also avoid oxidative damage. Providing the wherewithal to enhance elastin and collagen cross-linking, stimulate new vascular growth and to amplify the skin's tanning response to UV light are goals of the present invention. Another goal is to deliver copper in a form that is effective for reducing enlarged facial pores and scarring caused by acne. These goals are achieved with a therapeutic unit that binds copper with antioxidant plant pigments and chromophores and renders these copper-complexes capable of penetrating the skin; both concentrating the copper-complexes in and around sebaceous glands and also dispersing the copper-complex throughout the skin.

SUMMARY OF THE INVENTION

Biological systems are protected from environmental assaults, in part, by a variety of biochemical mechanisms designed to suppress oxidative reaction pathways. These antioxidant processes reduce exogenous pro-oxidant species and the endogenous secondary free radicals produced by these pro-oxidants. The most common source for generating free radicals in the skin is UV light, which splits hydrogen peroxide, a prevalent metabolic by-product, thereby generating the extremely reactive hydroxyl radical (.OH). The general environment in which people live and work also contains free radicals produced by combustion and other types of industrial chemical processes as well as cigarette smoking. The intensity of oxidative risks from our environment is increasing; this is particularly significant for skin because of its direct exposure to the environment. The skin employs various physiological mechanisms to repair oxidized macromolecules for renewal and recovery after oxidative injury. Interestingly, skin renewal can include the physiological production of superoxide radicals ($.O_2^-$) by phagocytic cells in order to destroy invading microorganisms. Although the superoxide radical is of itself not very reactive, it can react with transition metals such as ferrous iron ($Fe^{+2}$) and cuprous copper ($Cu^{+2}$) to generate the extremely reactive hydroxyl radical. Elimination of superoxide is primarily the responsibility of enzymes known as superoxide dismutases (SODs). The predominant form of SOD in the skin is the $Cu^{+2}/Zn^{+2}$ containing dimeric SOD enzyme. It is postulated here that increasing the amount of copper in the skin by the present method results in increased SOD activity, thereby reducing the amount of superoxide. To offset potentially harmful oxidizing side-effects, copper is applied to the skin in forms that can provide their own antioxidant protection; that is, by means of copper-complexed plant pigments and chromophores.

Another natural role for copper in the skin has to do with its binding to small peptides, notably the tripeptide GHK (glycyl-L-histidyl-L-lysine), which plays a key role in anti-aging and tissue repair processes. The $Cu^{2+}$ bound form of GHK (GHK-Cu) promotes the deposition of new collagen, and stimulates growth of new blood vessels in wound healing. GHK-Cu supports the activity of protease enzymes that remove scar tissue, replacing it with more normal-looking skin. GHK-Cu has also been reported to stimulate hair growth. It is postulated here that because the invention delivers copper in a non-toxic, bioavailable way, it promotes the formation of GHK-Cu and enhances skin repair, even in the absence of open wounds, as in acne, rosacea, etc.

Damaged or incomplete cross-linking of collagen and elastin can reduce the tensile strength of connective tissue. It has also been suggested by other investigators that such reduced cross-linking is the cause of spider veins: due to distension and thinning of blood vessel walls, which make dark venous blood visible through the skin. It is postulated here, that by increasing cross-linking as a result of the increased bioavailability of copper, the method can 1) reduce the visibility of under-eye dark circles, 2) improve tensile strength and elasticity of skin and thereby diminish the amount of skin lines and wrinkles, and 3) reduce the size of unattractive enlarged facial pores. It is further postulated that by binding the applied copper to antioxidant plant pigments and chromophores, the skin is afforded significant antioxidant protection.

The inflammatory processes of acne include defensive release of oxidants by neutrophils, which are released to destroy acne-producing microorganisms. The primary oxidant secreted by neutrophils is superoxide. It is postulated that the copper delivered by the invention increases SOD activity and reduces inflammation. It is also postulated that binding copper with antioxidant plant pigments and chromophores increases this activity. It has been suggested that seborrheic inflammatory conditions also play a role in excess oiliness of skin, producing a cosmetically unattractive shiny appearance. The anti-inflammatory benefits of copper, via SOD, and the copper-bound plant antioxidant, could reduce excessive oiliness in such cases.

The copper-antioxidant complex may be delivered in a liposomal dispersion, wherein the lipid shell of the liposome consists of lecithin. Although lecithin has been used for similar applications, the role of lecithin has been viewed strictly as an encapsulating material that facilitates the penetration of hydrophilic substances into the skin. The present invention is novel in recognizing that if the type of lecithin used is a structural combination of linoleic acid and phosphatidyl choline ("high linoleic acid lecithin"), then the liposome material itself may help to reduce acne symptoms. Liposomes of this type were made available by Rovi Cosmetics (ROVI GmbH & Co., Kosmetische Rohstoffe KG, Schluchtern, Germany), and are trade named Rovisomes. The present invention is therefore a novel advance for treating acne and acne-related symptoms, by combining the three types of benefits: copper ions, antioxidant plant pigments and chromophores, and a type of lecithin suitable for treating acne related skin complaints.

Another innovative aspect of the present invention has to do with controlled release of the copper, based on anticipated differences in pH as the liposome enters the skin. The copper atom is attached to the chlorophyllin by a metallic bond, so that the copper can be replaced by two protons: in other words, a more acidic pH favors dissociation of copper from chlorophyllin. A novel aspect of this method is therefore the formulation of the liposome dispersion at a slightly alkaline pH, typically 7.2-7.6: the copper-chlorophyllin stays intact as long as the liposome stays intact, but is expected to dissociate once the liposome enters the more acidic environment of the skin's outer mantle. It is postulated that this drop in pH as the liposomes pass into the skin play a vital role in the gradual release of copper from chlorophyllin, and, in fact, regulates delivery kinetics.

Formation of melanin is catalyzed by the enzyme tyrosinase, which helps convert the amino acid tyrosine to melanin. Reported research on genetically copper deficient mice has shown that direct addition of copper to their hair roots restores near normal levels of tyrosinase activity. This large increase in melanin production was shown to be due to the additional copper, not the production of additional tyrosinase molecules. Other reported experiments, conducted in copper-deficient sheep, likewise showed dramatic increases in pigmentation when copper was supplemented in the animals' diet. It is postulated that copper supplied to the skin using the present method may likewise enhance melanin production in human skin: thereby enhancing the tanning response and consequent protection against further sun damage. The simultaneous delivery of plant antioxidants is expected to provide additional photoprotection, reducing the oxidants produced by UV light. Onset of melanogenesis brought on by this invention may also prove to be of value in treating pigment-loss in diseases such as vitiligo.

In summary, the goals of the present invention are 1) to provide a carrier system for penetrating sequestered copper ions into the skin, 2) to effect stable, gradual release of the sequestered copper to make it available for its therapeutic benefits, and 3) to simultaneously release one or more antioxidants from the same carrier system. Many plant pigments and chromophores play active roles in protecting the plant against free radicals generated by activation of molecular oxygen or oxygen-containing metabolic by-products. The antioxidant nature of these pigments and chromophores is essential for survival of the plant and, often, these natural antioxidants contain a metal-ion that donates one or more electrons to the molecular orbitals involved in neutralizing free radicals. Specific examples of plant pigments possessing metal chelation and free radical scavenging properties include carotenoids, chlorophylls, anthocyanins, betalains and phycobilins, and the present invention is understood to include metal complexes of these pigments as well.

In one preferred embodiment, the carrier system is a liposomal dispersion containing lecithin liposomes of very small size, typically between 150-350 nanometers. $Cu^{+2}$ ions are loaded into the liposomes in the form of an aqueous solution of sodium-copper-chlorophyllin, which is a stable compound expected to release copper in a gradual manner. Chlorophyllin is itself a highly effective antioxidant, and is expected to neutralize the free radicals produced by reactions between $Cu^{+2}$ and hydrogen peroxide in the skin, and by UV light. Although sodium-copper-chlorophyllin is a stable compound, copper ion can be dissociated from chlorophyllin by the greater acidity of the skin compared with the pH of the liposome's internal environment. Copper can also be freed by an increase in the local temperature, brought on by direct heating of the skin surface or by mechanical means, e.g., ultrasound, or by imparting electromagnetic energy to the skin, as with a light source. Because copper ions bind readily to skin peptides and proteins, the success of this method depends on penetration of the copper-antioxidant complex to critical copper-binding sites. The combination of these particular liposomes, characterized by their high stability and small size, loaded with copper bound to an appropriate plant pigment or chromophore, is novel and essential to the invention.

The potential benefits of this method can be summarized:
1. Copper is needed for cross-linking of collagen fibers, which can prevent and reverse pre-mature skin aging brought on by excessive exposure to sunlight, environmental chemicals, smoking, and cleansing agents. Possible benefits are reduced lines and wrinkles. Another benefit is the reduction in size of enlarged pores. Improved cross-linking of collagen helps the healing of wounds and strengthening of weakened blood vessel walls, while also stimulating the deposition of new blood vessels. Benefits of the latter include the improvement of cosmetically unattractive conditions such as under-eye dark circles.
2. Copper is needed for formation of the superoxide removal enzyme, SOD. This reduces oxidative damage associated with inflammatory conditions, such as acne, as well as tissue destruction caused by free radicals generated by ultraviolet light. Simultaneous release of plant-derived antioxidants results in the destruction of a wide variety of free radicals, and also imparts anti-aging benefits. The liposome material is highly concentrated with linoleic acid, which is beneficial for acne sufferers.
3. Formation of copper-peptides, such as the tripeptide complex GHK-Cu, results in more complete wound healing and reduces scarring resulting from skin pathologies such as acne. GHK-Cu can stimulate hair growth in animal models and may exert similar benefits in humans.
4. Copper is an essential part of the melanin synthesizing enzyme tyrosinase, and the increased bioavailability of copper in the skin increases the activity of tyrosinase. This results in increased melanin production and enhanced skin tanning after sun exposure.

DETAILED DESCRIPTION OF THE INVENTION

We have described the importance of copper ions in skin biology, noting the role of copper as a part of the catalytic center for various enzymes and also its association with small peptides, such as GHK, modulating recovery of skin after injury. Whereas plant-derived chromophores such as chlorophylls and carotenoids have been recognized and used in skin care formulations for their antioxidant potential, binding copper ions with plant pigments and chromophores, specifically to deliver copper and enhance benefits of the copper thus applied, is new. Chlorophyll and chlorophyllin have been used to sanitize and deodorize wounds, to treat burns, blisters, and ulcerations, to treat psoriasis, and as additives to hair growth preparations. Copper ions, in such forms as copper sulfate, copper glycosides, copper sucralphate and copper gluconate, have had prior use as topical anti-inflammatory agents and in the treatment of spider veins, cellulite, poison ivy, as well as in antiviral compositions. Sodium-copper-chlorophyllin has been previously used as a photomodulation agent: whereby light energy absorbed by this compound, for example from a laser, is transferred to a neighboring, endogenous skin-cell chromophore, "energizing" the cell. The copper-chromophore may thereby function as a skin or hair growth stimulation agent. However, copper had not been assigned any active role in growth stimulation: it has been viewed only to stabilize the molecular structure of chlorophyllin.

Copper-chlorophyllin has been used previously as an internal deodorant in tablet form, in combination with proteolytic enzymes for the debridement and healing of ulcerative wounds (decubitus ulcers, colostomy openings, etc.) and as a colorant in dentifrice, bone cement, and certain dry foods. The oil-soluble copper-chlorophyllin and the water soluble sodium-copper-chlorophyllin have not been used topically in cosmetic, pharmaceutical, or cosmeceutical skin care products except for the limited use as a deodorant and wound healing additive to products used to treat deep, open wounds such as decubitus ulcers. In other words, neither forms of copper chlorophyllin have ever been used commercially in products as a treatment on intact skin.

It is postulated that copper-chlorophyllin has not been used in cosmetic products simply because copper-chlorophyllin is a dark-green pigment, even at low concentrations. For example, sodium-copper-chlorophyllin exhibits a dark-green color in water at 0.1%. Topical use products are typically uncolored or lightly colored with pigments to avoid staining of the skin. Green is, of course, not a natural skin tone. Studies have shown that the copper-chlorophyllin in the Rovisome liposome penetrates the skin and concentrations up to 0.1% by weight for very light skin and up to 0.5% by weight for very dark skin can be used topically (absorbed and not visibly evident), that is, they are cosmetically acceptable.

The novelty of the present invention is further supported by the following facts:
1. Based on history of use, one would not expect a priori the oil soluble or water soluble copper-chlorophyllin to penetrate intact skin or even skin affected by acne or rosacea;
2. Based on history of use, one would not expect that a low level of copper-chlorophyllin, for example, 0.1%-a level used as a colorant in dentifrice and foods, to show visible improvements in skin condition;
3. Based on history of use, one would not expect visible reductions in pore size, uneven skin coloring, and collagen-related changes in skin after twice daily use for only 2-3 weeks from this material;
4. Based on history of use, one would not expect significant antimicrobial activity for this material, such as we have demonstrated against *P. acnes*.

These findings are detailed in the next section.

The potential of sodium-copper-chlorophyllin as a copper-delivery agent, transferring chlorophyllin-bound copper to copper-dependent enzymes, is new, as is the concept of using chlorophyllin to reduce free radicals produced by free copper. Topically applied copper compounds do not of themselves penetrate the skin to a satisfactory extent, and the incorporation of copper-pigment and copper-chromophore complexes into small (0.15-0.35 micrometer) lecithin liposomes comes here with a new twist: the novelty is that using high linoleic acid content lecithin for the liposome wall has its own intrinsic beneficial effects on skin, namely, for treatment of acne and oily skin. Copper-pigment or copper-chromophore complex encapsulated in a linoleic acid-lecithin liposome is a new type of skin therapy, delivering copper ions, highly effective antioxidants and a therapeutic lipid.

We herein outline the preparation of such a "therapeutic unit", in an embodiment of the invention that utilizes sodium-copper-chlorophyllin as the copper-chromophore complex. Plant chromophores invariably possess a metal-ligand binding site. In natural chlorophyll this binding site is occupied by a magnesium atom. Copper can be substituted for magnesium by first treating the chlorophyll with an acid, thereby replacing the magnesium with two hydrogen atoms, and thereafter replacing the hydrogen with copper by alkaline hydrolysis with a copper salt solution. Alkaline hydrolysis with a sodium salt also opens the cyclopentone ring of chlorophyll and replaces the ester groups with sodium, creating sodium-copper-chlorophyllin.

Liposomes loaded with NaCu-Chlorophyllin were prepared by Rovi Cosmetics (Schluchtern, Germany). Composition (by weight) consisted typically of lecithin (10.00%), sodium-copper-chlorophyllin (5.00%), ethyl alcohol (3.33%), Phenonip (0.50%), and water buffered with potassium dihydrogen phosphate. The pH of the "raw" liposome dispersion ranged from 6.5 to 8.5. The material was stored in a dark, cool (5° C.) area until used in a treatment composition as detailed below.

In one embodiment of the invention, the raw liposomal dispersion was formulated into a cosmeceutically acceptable gel of the following composition:

| CHLOROPHYLLIN TREATMENT GEL; FORMULA #28-145 | |
|---|---|
| Ingredient | % w/w |
| Carbopol 940; 2% dispersion | 55.00 |
| 1,3-Butylene Glycol | 4.00 |
| Ethanol SD 40, 190 Proof | 3.50 |
| Sodium Lactate, 60% (PatlacNAL) | 1.60 |
| Pentylene Glycol (Hydrolite-5)) | 4.00 |
| Phenoxyethanol | 0.75 |
| Sodium Hydroxide solution, 25% | 1.50 |
| Rovisome I* (Rovi; Schluchtern, Germany) | 2.00 |
| Deionized Water | 21.70 |
| Total | 100.00 |

*Rovisome I is a custom liposomal dispersion containing 5% w/w sodium-copper-chlorophyllin in a high linoleic acid lecithin shell.
The final concentration of sodium-copper-chlorophyllin in the above treatment gel is 0.1% w/w. The pH of the gel was typically adjusted to between 7.2-7.6; in the above example with NaOH. The following studies were conducted to evaluate the effectiveness of such compositions.

Study 1

In this clinical trial, an aqueous gel base containing the dispersion of lecithin liposomes and 0.10% by weight sodium-copper-chlorophyllin was evaluated for its effectiveness in treating large pores on the nose and/or cheeks, acne, oiliness of skin, and blotchiness (uneven reddish skin color) of ten subjects with mild to moderate acne. The gel was applied to the nose and cheeks twice daily for four weeks. Skin condition was evaluated by both the patients themselves and by an expert clinical grader. Methods of clinical evaluation included visual examination (counting of acne lesions and enlarged pores, visible skin oiliness and smoothness of skin texture) and measurements of oiliness using Sebutape®, and digital photography. Evaluations were carried out at the start of the study and after four weeks of treatment. Results: After four weeks of treatment most of the ten patients had a decrease in skin oiliness (8/10), most had fewer enlarged pores (9/10), a few had less acne (3/10), less sebaceous thickening of the skin (4/10), and smoother skin (3/10). In their self-assessment, all ten patients felt that their skin condition improved, especially with regard to reduced oiliness, pore size and overall appearance. Sebutape measurements were made at four facial sites: the right side and left side of the forehead, plus the nose and the chin. A global parameter of overall skin oiliness was calculated by summing these four Sebutape measurement values for each patient at the start of the study, and again at two weeks and at four weeks into the treatment. The Sebutape results showed an average 9% reduction in the amount of skin-surface oil after two weeks and an average reduction of 13% at four weeks; the latter is statistically highly significant. It was also noticed that most of the patients had reduced inflammation (redness), particularly one patient with acne-rosacea. Overall, the study indicated that the treatment results in dramatic reduction of inflammation.

Study 2

This study was conducted at a different clinical research site, and again examined the benefits of a twice-daily facial application of the 0.10% sodium-copper-chlorophyllin gel. Ten subjects, men and women 18-30 years of age, were enrolled in the study. Each subject had mild to moderate acne, with large, visible pores on the nose and/or cheeks, oily skin and blotchy skin coloration. Clinical grading of enlarged facial pores, oiliness and blotchiness were performed during the panelists' initial visit and repeated after three weeks of treatment. Acne was evaluated by counting inflammatory lesions (papules, pustules and nodules) and non-inflammatory lesions (open and closed comedones) for the full face (forehead, left and right cheeks and chin) at the initial visit and after three weeks. The subjects also provided self-assessment diary data of their skin condition throughout the study. Results: The following table summarizes the percentage of statistically significant improvements determined at the three-week time point compared with pre-treatment values, as determined by clinical grading.

| Attribute | Percentage Improvement |
| --- | --- |
| Oiliness | −36.1% |
| Enlarged pores | −21.9% |
| Blotchiness | −26.8% |
| Closed Comedones | −28.3% |
| Global Acne Score | −13.0% |
| Face Overall | −18.6% |

The majority of subjects (8/10) noted various degrees of improvement in their own skin condition, mainly with respect to reduced oiliness, visibility of pores and evenness of color and texture. Digital photographic analysis utilizing the VISIA® clinical grading system calculated significant reduction in pores, acne-related porphyrins, and improvement in overall skin evenness.

Study 3

A small clinical study was carried out using 5 panelists, to investigate whether sodium-copper-chlorophyllin enhances skin tanning following UV-light irradiation. We were in effect testing whether the gel preparation increases tyrosinase activity by increasing the availability of copper in the skin. The net effect of sodium-copper-chlorophyllin on tanning was somewhat unpredictable, because even if copper stimulates melanogenesis by increasing the activity of tyrosinase, the impact of UV may be reduced, because chlorophyllin is a strong UV absorber (sunscreen) and chlorophyllin is also a strong antioxidant, expected to reduce erythema. We therefore compared the degree of tanning produced by the sodium-copper-chlorophyllin (0.10%) against the tanning produced by an identical preparation of sodium-magnesium-chlorophyllin (0.10%) (The magnesium-complex of chlorophyllin corresponds to the actual plant-derived form of chlorophyll, and has approximately the same UV-absorbance and sunscreen attributes as the copper form). Therefore, any increase in melanin formation by the copper-complex over that for the magnesium-complex would be due to copper.

Five people, 18-65 years of age, participated in the study. All were Fitzpatrick skin type III or IV; that is, all five subjects had substantial tanning capability. The minimal erythemal dose (MED) was determined on the lower back of each subject over the first two days of the study. Thereafter 200 microliters of a treatment gel containing 0.10% by weight of either sodium-copper-chlorophyllin or sodium-magnesium chlorophyllin in a liposomal dispersion as described in Studies 1 and 2 was applied to 1 $cm^2$ sites on the lower back and covered with a semi-occlusive skin patch. The gels were re-applied and patched daily for 5 consecutive days to randomly assigned and coded sites on either side of the lower back. After 5 days, the final patches were removed and the test areas were irradiated with simulated solar light, at dosages of either 1.5 or 2.0 MED. Two untreated sites were also irradiated at 1.5 and 2.0 MED for comparison. The irradiated sites, treated and control, were visually graded for "Darkness" and "Degree of Tanning" at 4 days and 7 days post-irradiation. Darkness scores refer to total skin pigment (hemoglobin and melanin), whereas Tanning scores refer more to melanin. Treated areas of each subject were photographed at 7 days after irradiation using macrophotographic techniques, with and without polarized light. Results: The Darkness ranking (in which the sites are ranked on a scale of 1-6, with 1 being the darkest), resulted in the following average scores:

| Treatment | Average Darkness Score | Std. Dev. |
| --- | --- | --- |
| Untreated | 3.95 | 2.03 |
| Mg-Chlorophyllin | 3.55 | 1.60 |
| Cu-Chlorophyllin | 2.80 | 1.47 |

Given the small sample size, the differences amongst the three types of sites are not statistically significant, but directionally the scores show the copper-chlorophyllin treated sites to be the darkest.

The Degree of Tanning scores proved to be more interesting:

| Treatment | Average Tanning Score | Std. Dev. |
| --- | --- | --- |
| Untreated | 5.55 | 1.48 |
| Mg-Chlorophyllin | 5.25 | 0.98 |
| Cu-Chlorophyllin | 6.15 | 1.84 |

(Degree of Tanning is ranked on a scale: 0 = very light tan and 10 = very deep tan).

This study, although involving only 5 subjects, showed the expected directional differences in the tanning response, in that 1) the magnesium-chlorophyllin treated sites had less tanning than the untreated sites, presumably because of the UV-light absorption and antioxidant protection afforded by chlorophyllin, and 2) the presence of the copper atom gave a substantial boost in the tanning response compared to that seen with Mg-chlorophyllin, presumably showing the copper effect.

Study 4

The unexpected result that the sodium-copper-chlorophyllin gel used in the above described clinical studies reduced acne-associated inflammation and porphyrins led us to propose that we were observing a copper-mediated antimicrobial effect on *Propionibacterium acnes*. To test this hypothesis, a "kill rate" test against *P. acnes* was conducted at a microbiological testing laboratory. The study compared the antimicrobial properties of the treatment gel containing 0.1% sodium-copper-chlorophyllin against the same gel composition with 0.1% sodium-magnesium-chlorophyllin. Antimicrobial activity of the two gels was determined using the standard methodology of counting the number of organisms on test plates covered with the respective gels after 1 hour and 24 hours of incubation. The kill rate is calculated as the logarithmic reduction in the concentration of organisms when compared with the concentration of organisms in the original inoculation material. Results are summarized in the following table:

| Treatment Gel with 0.1% NaCu Chlorophyllin | | | |
|---|---|---|---|
| Organism | Inoculum Level | Average | Log Reduction |
| P. acnes 1 hour | $2.95 \times 10^5$ | No Growth | 5.47 |
| P. acnes 24 hours | $2.95 \times 10^5$ | No Growth | 5.47 |

| Treatment Gel with 0.1% Na Mg Chlorophyllin | | | |
|---|---|---|---|
| Organism | Inoculum Level | Average | Log Reduction |
| P. acnes 1 hour | $2.95 \times 10^5$ | 6,500 | 1.66 |
| P. acnes 24 hours | $2.95 \times 10^5$ | 2,000 | 2.17 |

A log reduction of 2.17 obtained with the sodium-magnesium-chlorophyllin gel is considered ineffective antimicrobial activity, and may in fact be due to just the gel base itself. On the other hand, the practically total kill of *P. acnes* seen with sodium-copper-chlorophyllin gel suggests very strongly that the copper exerts significant antimicrobial activity, and we propose it is the copper that dissociates from chlorophyllin that is responsible for the reduction of acne symptoms seen in the clinical studies.

What is claimed is:

1. A monomodal method for reducing the appearance of one or more clinical signs of premature skin aging, the clinical signs of premature skin aging being one or more of skin wrinkling, sagging, roughness, blotchiness and uneven pigmentation, the method consisting essentially of the step of: applying to and leaving on an area of human skin presenting with one or more clinical signs of premature skin aging a topical composition comprising either or both of copper chlorophyllin and sodium copper chlorophyllin in an aqueous solution, the copper chlorophyllin and/or sodium copper chlorophyllin being present in a concentration non-staining to human skin and between 0.0001 and 0.5% by weight of the composition, the aqueous solution contained within liposomes, the liposomes having a lecithin shell having a fatty acid component, more than 50 wt-% of the fatty acid component being linoleic acid, the liposomes having an average diameter between 150 to 350 nanometers, and wherein the liposomes are dispersed in a dermatologically-acceptable carrier and further wherein the topically-applied composition is administered at least once daily for a period of at least two weeks.

2. The method of claim 1 wherein the dermatologically-acceptable carrier contains a skin penetration enhancing ingredient.

3. The method of claim 2 wherein the skin penetration enhancing ingredient is selected from the group consisting of propylene glycol, butylene glycol, pentylene glycol, isopentyl glycol, ethoxydiglycol, dimethyl isosorbide, acetamide MEA, tetrahydropiperine, PEG glyceryl ethers, Levomenol, N-methyl-2-pyrrolidone, dimethyl sulfoxide and methyl sulfone.

\* \* \* \* \*